United States Patent [19]

Bolander et al.

[11] Patent Number: 4,743,259

[45] Date of Patent: May 10, 1988

[54] USE OF DEMINERALIZED BONE MATRIX IN THE REPAIR OF SEGMENTAL DEFECTS

[75] Inventors: Mark E. Bolander, Washington, D.C.; Gary Balian, Charlottesville, Va.

[73] Assignee: The University of Virginia Alumni Patents Foundation, Charlottesville, Va.

[21] Appl. No.: 924,513

[22] Filed: Oct. 29, 1986

[51] Int. Cl.$^4$ .................. A61F 2/28; A61K 35/12; A01N 1/02

[52] U.S. Cl. .................................. 623/16; 623/66; 424/95; 427/2; 514/2; 514/21

[58] Field of Search .............. 623/16, 66; 427/2; 514/2, 21; 424/95

[56] References Cited

U.S. PATENT DOCUMENTS

| | | | |
|---|---|---|---|
| 4,294,753 | 10/1981 | Urist | 424/95 X |
| 4,378,803 | 4/1983 | Takagi et al. | 623/66 X |
| 4,434,094 | 2/1984 | Seyedin et al. | 424/95 X |
| 4,440,750 | 4/1984 | Glowacki et al. | 424/95 |
| 4,455,256 | 6/1984 | Urist | 424/95 X |
| 4,608,199 | 8/1986 | Caplan et al. | 424/95 X |
| 4,609,551 | 9/1986 | Caplan et al. | 623/16 X |
| 4,619,989 | 10/1986 | Urist | 424/95 X |
| 4,620,327 | 11/1986 | Caplan et al. | 623/16 X |
| 4,627,982 | 12/1986 | Seyedin et al. | 424/95 |
| 4,681,763 | 7/1987 | Nathanson et al. | 424/95 |

OTHER PUBLICATIONS

Bolander et al., "Demineralized Bone Matrix: Use in Repair of Segmental Defects", 29th Annual ORS, Anaheim, CA, Mar. 8-10, 1983.
Bolander et al., "Demineralized Bone Matrix: Use in Repair of Segmental Defects", The J. Bone and Joint Surgery, vol. 7, No. 2, Summer 1983.

*Primary Examiner*—Richard J. Apley
*Assistant Examiner*—Alan W. Cannon
*Attorney, Agent, or Firm*—James Creighton Wray

[57] ABSTRACT

A process of grafting material from milled bone is disclosed which comprises augmenting the bone protein of a first quantity of milled bone by dialyzing from solution guanidine-extracted bone proteins from a second quantity of milled bone and adding the extracted proteins to the first quantity of milled bone. Next, unbound proteins are removed and then the augmented milled bone is lypohilized, after which the augmented milled bone is coated with anti-coagulated plasma containing plasma proteins. Any unbound plasma protein is removed from the coating by rinsing.

1 Claim, 4 Drawing Sheets

USE OF DEMINERALIZED BONE MATRIX IN THE REPAIR OF SEGMENTAL DEFECTS

INTRODUCTION

Bone is one of the most frequently transplanted tissues in humans, and is routinely used for the repair of skeletal defects from trauma, neoplasm, and infection. Two mechanisms aare postulated to account for bone deposition after bone graft procedures: first, autogenous grafts retain viable osteoblasts that participate in bone formation, second, both autografts and allografts provide the lattice for the deposition of bone by the process of 'creeping substitution' (14). Recent investigation of bone formation in response to demineralized bone grafts demonstrates that a third mechanism, induced osteogenesis, also contributes to bone formation. Intensive laboratory investigations by Urist, Reddi, and others (8,11,16,18,21,26,28,29,38,39,40,42), demonstrated the effect of demineralized bone matrix or bone morphogenetic protein in bone induction. However, the rate, pattern, and ultimate degree of repair of defects in bone grafted with decalcified bone matrix remains unknown. This lack of knowledge prevents the successful application of the principle of bone induction to clinical situations.

Urist et al. (39,43,44) have demonstrated that the active components of the demineralized bone matrix are the low molecular weight proteins or bone morphogenetic protein. Anastassiades et al. (1), Tokaoka et al. (37) and Hanamura et al. (15) have further demonstrated that these low molecular weight proteins can be extracted from demineralized bone with guanidinium hydrochloride. Sampath and Reddi (30,31) have shown that although, after separation, neither the extracted proteins nor the residue are capable of bone induction by themselves, they can be recombined to reconstitute a bioactive, bone inducing matrix. In addition to bone matrix proteins, fibronectin, a cell surface protein which is also present in plasma where it is referred to as plasma fibromectin (49), has been demonstrated on the surface of demineralized bone matrix particles in subcutaneous implants of demineralized bone matrix. Localization of fibronectin on the surface of the particles has been shown to be necessary for demineralized bone matrix induced endochondral ossification (45,46).

This study was directed towards answering two questions: first, what are the characteristics of the healing process when demineralized bone matrix is used to graft a segmental bone defect and how does this compare with the healing of an autologous cancellous bone graft? Second, is it possible to augment or accelerate the healing of a demineralized bone matrix graft by augmenting the concentration of guanidinium extracted proteins on the demineralized matrix? For this study, autologous cancellous bone from the iliac crest, demineralized bone matrix prepared as previously described by others (22, 23), and demineralized bone matrix augmented with guanidinium extracted proteins were used as grafts in segmental defects. The effect of these materials on graft healing was evaluated by histology, radiography, and torsional strength testing.

SUMMARY OF THE INVENTION

MATERIALS AND METHODS

Preparation of Demineralized Bone Matrix Grafts.

Demineralized bone matrix was prepared from diaphyseal segments of femora and tibia harvested from freshly sacrificed adult New Zealand White rabbits. All soft tissue was removed and the bones were washed in sterile deionized water. Cleansed bones were extracted for 1.5 hours in a 1:1 chloroform-methanol mixture (30 ml/g bone), dried overnight, milled in a Wiley mill, sieved to between 72 and 850 microns and decalcified in 0.6M HCl for three to four hours (50 ml HCl/g bone). The resultant powder was rinsed with serial changes of sterile deionized water to bring the pH to 3.5 or above and then lyophilized. This preparation was completed under sterile conditions at 2° C. except for milling which was performed by mixing the dry bone with crushed dry ice during the milling process. Lyophilized specimens were stored at −70° C. Three samples from each preparation of demineralized bone matrix were cultured. No specimen demonstrated bacterial or fungal contamination. Demineralized bone matrix was shown by histological examination to induce bone in intramuscular implants.

Preparation of Augmented Demineralized Bone Matrix Grafts.

Proteins soluble in guanidinium hydrochloride were extracted from three grams of demineralized bone matrix at 4° C. for sixteen hours in 90 ml 4M guanidinium hydrochloride buffered with 50 mM Tris, pH 7.4 containing protease inhibitors (0.5 mM phenylmethyl-sulfonyl fluoride, 5 mM N-ethylmaleimide, 5 mM benzamidine, 0.1M 6-aminohexanoic acid)(30). The supernatant containing the guanidinium hydrochloride soluble factors was separated from the residue by centrifugation at 30,000 g. The supernatant was then combined with three grams of demineralized bone matrix-graft, prepared as described above, by placing the two together in dialysis tubing (Spectrophor, exclusion limit 3,500 daltons) and dialyzed against deionized water for sixteen hours. Protease inhibitors were added to the first two dialysis changes. After dialysis, the demineralized bone matrix graft was separated from the supernatant by centrifugation at 30,000 g and lyophilized. This material, consisting of three grams of demineralized bone matrix and the guanidinium hydrochloride soluble proteins from another three grams of demineralized bone matrix, was called augmented demineralized bone matrix. A small aliquot of the guanidinium hydrochloride extract was removed prior to recombination with demineralized bone matrix, dialyzed separately, and prepared for sodium dodecyl sulfate polyacrylamide gel electrophoresis and amino acid analysis.

Weiss and Reddi (45,46) have ascribed a critical function to fibronectin, a circulating protein with collagen binding, adhesive, and chemotactic properties (10,48). In the early phases of bone formation, fibronectin mediates the attachment of cells to the demineralized bone matrix (45,46). Preliminary evaluation of demineralized bone matrix graft healing demonstrated that pretreatment of the demineralized bone matrix with either citrated plasma or with fibronectin accelerated the appearance of bone formation on radiographs and enhanced the continuity of the bone that was formed. Based on these observations, all demineralized bone matrix and augmented demineralized bone matrix was pretreated with autologous citrated plasma prior to use as a graft. After the induction of anesthesia, twelve ml. of blood were obtained by arterial puncture. Under sterile conditions, the blood was anticoagulated with 1.5 ml citrate and cells were separated by centrifugation. The plasma was passed over 0.2 grams demineralized bone matrix or augmented demineralized bone matrix packed in a 0.7×10 cm column. The column was then rinsed with several column volumes of Lactated Ringers solution and the demineralized bone matrix removed. As reported by Weiss and Reddi (46), plasma fibronectin specifically binds to demineralized bone matrix and can be removed by elution with 6M urea and identified by sodium dodecyl sulfate polyacrylamide gel electrophoresis. The demineralized bone matrix graft, after treatment with autologous plasma, was called fibronectin coated demineralized bone matrix or augmented fibronectin coated demineralized bone matrix.

Harvesting of Autologous Cancellous Iliac Crest Bone Grafts.

Autologous cancellous bone was harvested from the rabbit iliac crest at the time of grafting. A full thickness portion of the rabbit posterior iliac crest measuring approximately five square centimeters was resected. The internal and external tables of the excised segment of ilium were separated and the cancellous bone was harvested with a curette. This graft was always used immediately after harvesting.

Segmental Defect Model.

The model we used was a segmental ulnar defect (2,50). New Zealand White rabbits were anesthetized with intravenous pentabarbitol. Both forelegs were shaved, sterilized with betadine solution, and draped with sterile towels. An incision was made directly over the ulna, which was exposed by dissection of the surrounding muscles. A two centimeter section of the ulna and surrounding periosteum was removed so that the distal end of the defect was one centimeter proximal to the radiocarpal joint.

To allow a valid comparison of the strength of different graft materials as healing occurred, we compared grafts placed in the right with grafts placed in the left forelegs of the same animal (25). Forty-eight New Zealand White rabbits, all greater than one year old and from a single supplier, were divided into four groups (Table 1).

The graft material, either autogenous cancellous bone graft, fibronectin coated demineralized bone matrix graft, or augmented fibronectin coated demineralized bone matrix graft, was placed in the defect and held in position by suture of the muscle and fascia over the graft. Sufficient autogenous graft was used to completely pack the defect. 0.2 grams of fibronectin coated demineralized bone matrix or augmented fibronectin coated demineralized bone matrix was used, as this filled the defect to the same extent as the autograft. The skin was then closed over the muscle and fascia with wire sutures, and bacitracin ointment was applied to the wound. No other antibiotics were given.

There were no intraoperative deaths. One animal in Group II developed a respiratory infection and died three days after surgery. Three other respiratory infections were successfully treated with antibiotics. No animal developed fracture of the radius.

Evaluation of Healing.

Grafts were evaluated by radiography, by mechanical testing and by histology. All animals were x-rayed at the time of surgery, at six and twelve weeks after surgery and were sacrificed at twelve weeks. Ulnas were harvested, x-rayed after all soft tissue was removed, photographed, and potted in methylmethacrylate in preparation for mechanical testing. Because the rabbit ulna has a slight curve, all ulnas were carefully mounted with the healed graft coaxial with the axis of the torsion tester. The distance between the pots was kept constant at 3.5 cm. Ulnas were tested to failure in a Burstein torsion tester connected to a Hewlett Packard Model 1741A oscilloscope (5,47). Torque versus angular deformation curves were displayed on the oscilloscope and photographed. Maximum angular deformation, maximum torque, and energy absorption prior to failure were calculated from torque-angular curves (5,8,47). The mean value and standard deviation for these mechanical properties were calculated for the fibronectin coated demineralized bone matrix grafted ulna and the opposite ulna in each group. Differences between the values for torque, angular deformation and energy absorption for the fibronectin coated demineralized bone matrix grafted ulna and the opposite ulna, either autograft, augmented fibronectin coated demineralized bone matrix graft, or normal ulna, were calculated for each animal and evaluated by Duncan's multiple range test (7). Major fragments were decalcified, sectioned, stained and examined microscopically.

RESULTS

Figure 1:
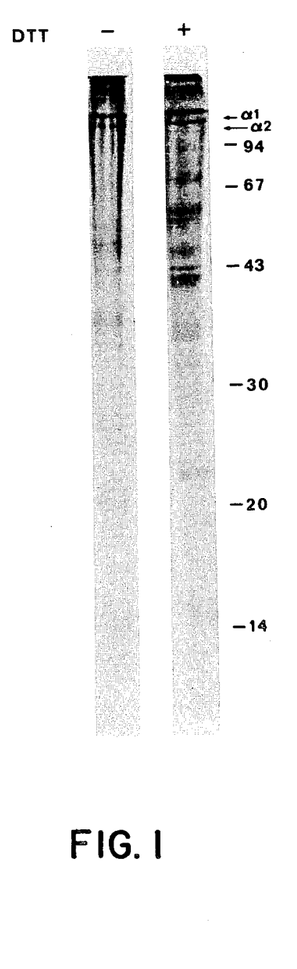

Biochemical Analysis: The demineralized bone matrix, the guanidinium hydrochloride extracted proteins, and the residue remaining after guanidinium extraction were subjected to amino acid analysis (Table 2). The high glycine and hydroxyproline content in both the demineralized bone matrix and the residue indicates a high percentage of collagen. The marked decrease in these amino acids as well as hydroxylysine in the guanidinium hydrochloride extract and the increase in leucine, isoleucine and tyrosine indicate a lower collagen concentration and a corresponding increase in the concentration of non-collagenous proteins. Guanidinium extracted low molecular weight proteins were also analyzed by sodium dodecyl sulfate polyacrylamide gel electrophoresis (FIG. 1). Electrophoresis of the guanidinium hydrochloride extract shows the presence of the $\alpha 1$ and $\alpha 2$ chains of collagen in addition to proteins ranging in size between approximately 14 and 97 kilodaltons. The molecular weight range of the proteins in this guanidinium hydrochloride extract includes bone morphogenetic protein (18 kilodaltons) which has been identified by Urist et al. (43,44) and shown to have osteoinductive capacity when combined with extracted matrix (30).

Figure 2:
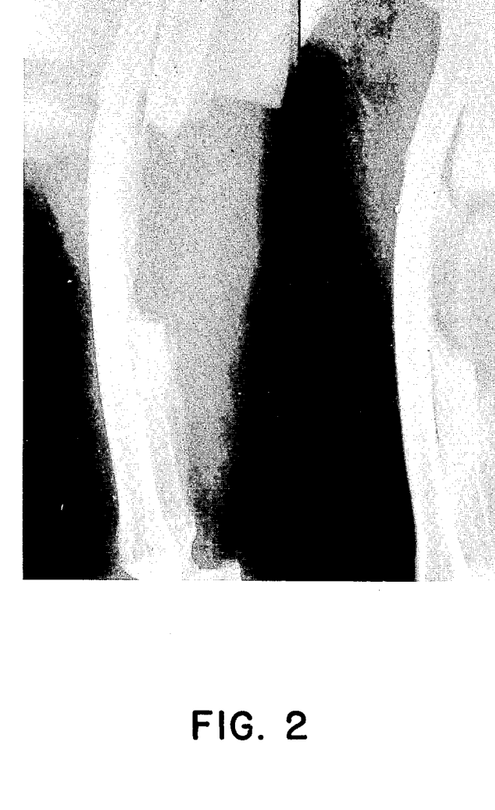

Pretreatment of demineralized bone matrix grafts with citrated plasma: In preliminary grafting procedures, demineralized bone matrix grafts often failed to heal or healed incompletely (FIG. 2a). Extensive gaps were seen on early radiographs where the grafts failed to bridge the ulnar defect. Pretreatment of demineralized bone matrix grafts with autogenous citrated plasma which contains fibronectin (fibronectin coated demineralized bone matrix grafts), resulted in accelerated healing of the defect (FIG. 2b).

Radiographic Evaluation of Healing: Radiographs documented the formation of bone and subsequent remodeling of the graft in all animals. FIG. 3 illustrates this in an animal from Group II.

The radiographs showed no difference between the fibronectin coated demineralized bone matrix grafts and autografts, or between fibronectin coated demineralized bone matrix grafts and augmented fibronectin coated demineralized bone matrix grafts at six and twelve weeks. Ungrafted ulnas (Group IV) formed large masses of callus at the cut end of the defect. In all Group IV animals this callus failed to bridge the defect and in most the proximal callus fused to the radius.

Radiographs were taken after harvest of the ulnas at twelve weeks (FIG. 4a–h). Although there are obvious differences between the grafts in different animals, radiographic diferences between the right and left ulna in each animal are few. The graft cortex is clearly thinner than the normal cortex (4a and 4b), and there are numerous cortical irregularities.

Gross Appearance of Ulnas at the Time of Sacrifice: The gross appearance of the grafts at sacrifice paralleled their radiographic picture. In all cases the graft completely bridged the defect. All grafts were covered with fibrous tissue, continuous with normal periosteum. No consistent differences could be identified between autografts, fibronectin coated demineralized bone matrix grafts, or augmented fibronectin coated demineralized bone matrix grafts in either size, shape or continuity of the graft with the cortex of the adjacent ulna.

Histologic Evaluation of Healing: Hematoxylin and eosin stained sections of grafted ulnas from each of the four groups were examined microscopically and compared. Only one remnant of the original graft, a highly birefringent piece of lamellar bone, was seen in a fibronectin coated demineralized bone matrix graft. With the exception of this fragment of demineralized bone matrix graft, the sections for all grafted ulnas were very similar microscopically. An irregular cortex composed of woven bone was typical for all grafts (FIG. 5). The medullary canal was well formed in all grafts and populated by marrow elements that appeared normal. Little trabecular bone was seen in the intramedullary cavity, consistent with normal ulnar anatomy. The junction of the original defect with the graft was easily identified. Woven bone abutted the dense lamellar bone of the original cortex (FIG. 5c), separated by a single cement line. Examination by polarized light failed to demonstrate any collagen fibers crossing this junction between the newly formed woven bone and lamellar bone of the cortex. When compared to the cortex remote from the defect, the lamellar bone of the original cortex in the region of the defect had a large number of haversian canals of increased size. A significant amount of subperiosteal bone was seen in the vicinity of the graft even though the periosteum was not elevated at the time of surgery. The cortex of the graft was continuous with this subperiosteal bone, rather than with the original cortex.

Non-grafted ulnas did not successfully heal across the defect and, therefore, no mechanical testing was performed. Histologic sections of non-grafted ulnas from Group IV showed only limited new bone formation in the vicinity of the cut end of the defect.

Figure 6:
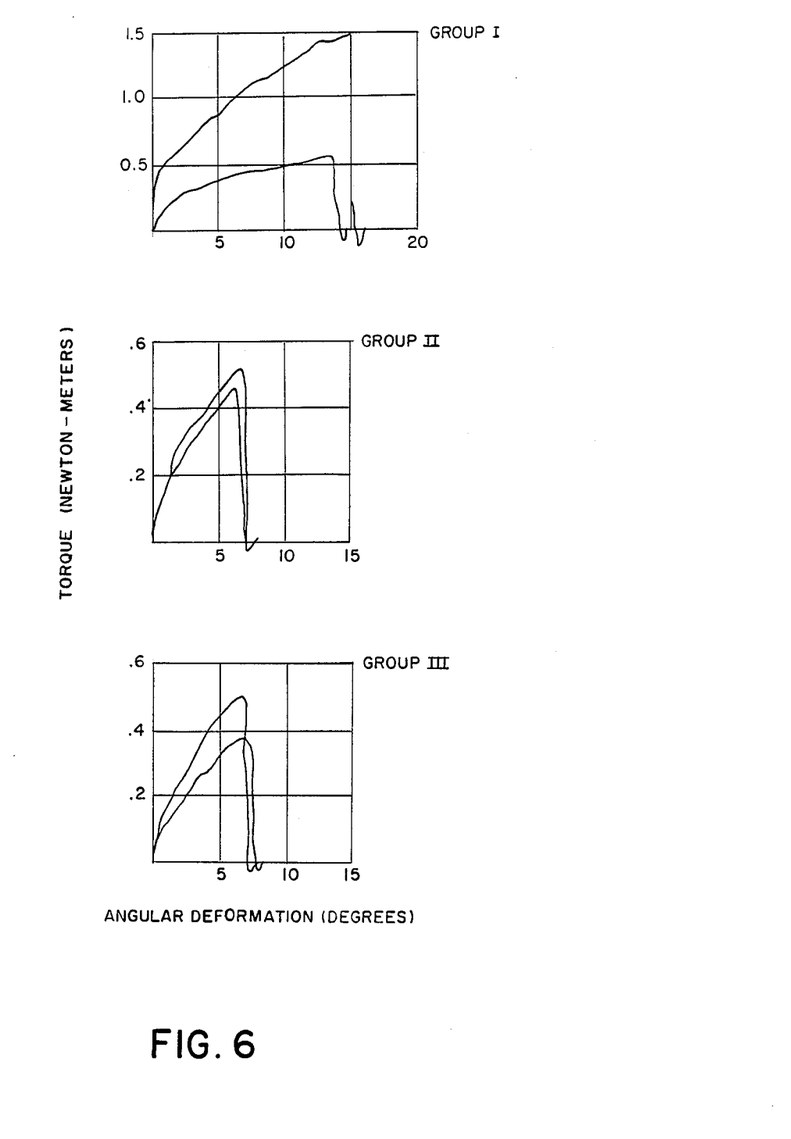

Mechanical Tests: Torsional failure of all specimens occurred in the distal graft-ulna junction, producing a spiral fracture with one or more butterfly fragments. Typical load-deformation curves for an animal from each group are shown in FIG. 6. Mean values of maximum torque, maximal angular deformation, and energy absorption at failure for the ulnas in each group, as well as mean differences for each group and a summary of the statistical analysis is given in Table 3.

Based on the Duncan's Multiple Range Test analysis, the fibronectin coated demineralized bone matrix grafted ulnas fail with significantly less torque and after significantly less angulation than normal ulnas. Likewise, the energy absorbed at the time of fracture is significantly less for the fibronectin coated demineralized bone matrix grafted ulna than for the normal ulna. Fibronectin coated demineralized bone matrix grafted ulnas and the autografted ulnas were statistically indistinguishable. Augmentation of the fibronectin coated demineralized bone matrix graft with guanidinium hydrochloride extracted proteins significantly increased energy absorption and angulation at failure relative to the non-augmented fibronectin coated demineralized bone matrix, but it did not enhance torque values significantly.

DISCUSSION

Autogenous cancellous bone from a source such as the iliac crest is generally considered to be the best material for bone grafting (6,20). Allogenic banked bone is advocated as an alternative to autograft, but the effectiveness of this graft is often compromised by nonanion, fatigue fracture, and both clinical and histologic evidence of graft resorption (4). Based on animal studies, several authors have considered the possible use of decalcified bone matrix as a graft in clinical situations for repair of segmental defects (3,8,18,38). Although these reports suggest certain assumptions about the physical characteristics of the healed grafts, an evaluation of the mechanical properties of the newly formed bone, correlated with observed histological and radiographic changes, is necessary to evaluate the usefulness of demineralized bone grafts.

Figure 3A:
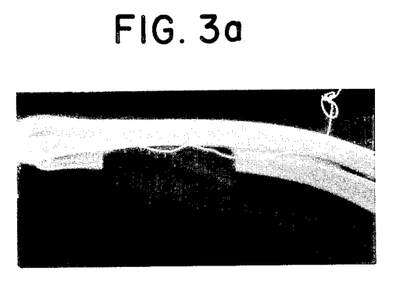
Figure 3B:
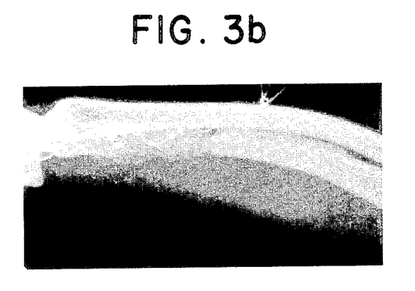
Figure 3C:
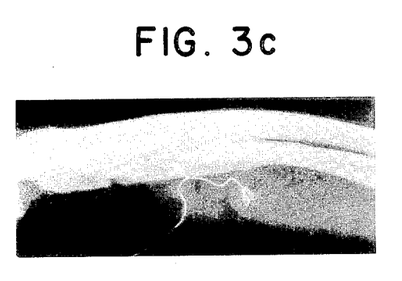
Figure 3D:
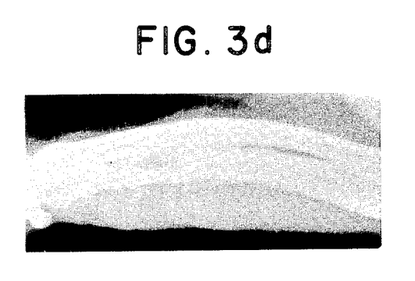
Figure 3E:
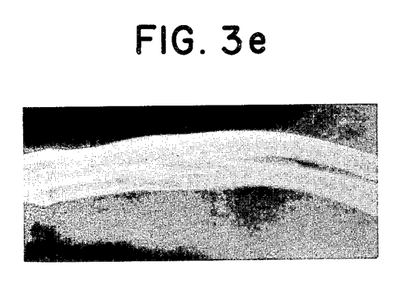
Figure 3F:
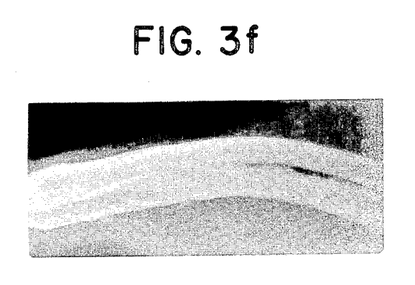
Figures 4A, 4B, 4C, 4D, 4E, 4F, 4G, 4H:
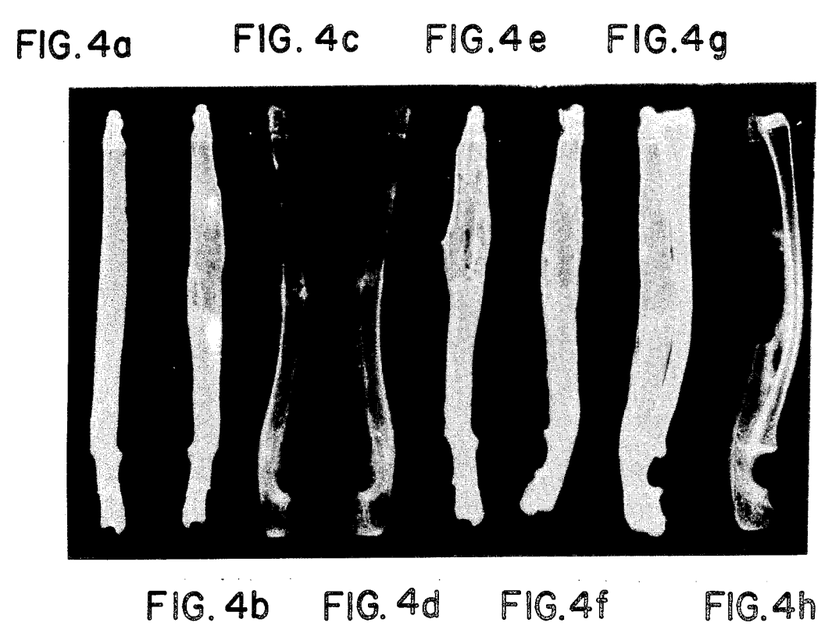
Figure 5A:
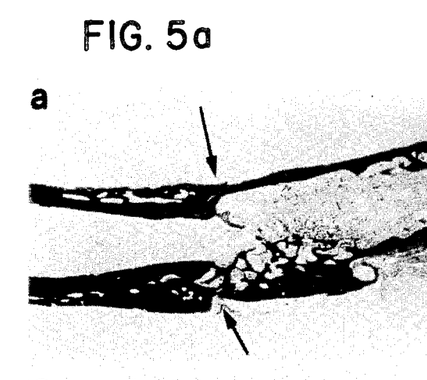
FIG. 5: Photomicrograph showing a fibronectin coated demineralized bone matrix graft and its proximal junction with the normal cortex, twelve weeks after grafting. Sections were stained with hematoxylin and eosin and viewed with either transmitted light (a, c) or polarized light (b, d). Magnifications: a and b: 5×, c and d: 10×. The high power view of the junction between the graft and the original bone shows viable cells and failure of collagen fibers to cross the cut end of the defect indicated by the arrows.
Figure 5B:
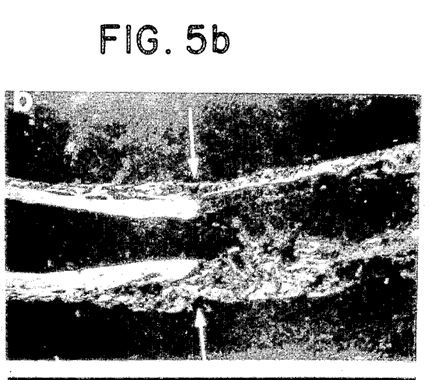
Figure 5C:
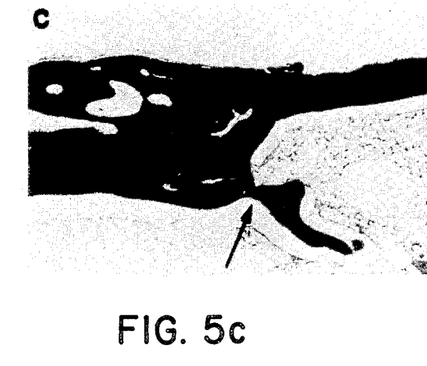
Figure 5D:
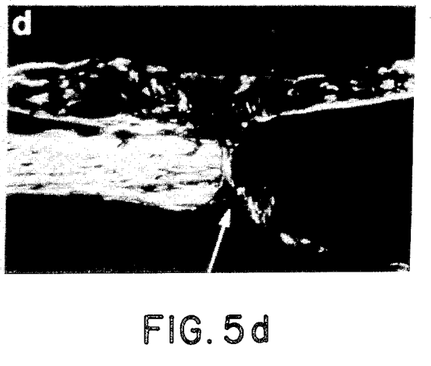

Our histologic studies of fibronectin coated demineralized bone matrix graft implants in muscle (data not shown) showed a sequence of events leading to bone formation that was identical to the sequence reported by several other laboratories (26,27). Radiographs of the ulnar defect taken at different times after surgery showed calcification of the graft and subsequent maturation to osseous tissue (FIG. 2b, FIG. 3a,c,e). This supports the hypothesis that the fibronectin coated demineralized bone matrix grafts do not heal by a process of creeping substitution, but instead heal through calcification and subsequent ossification of the entire similar to the process described in nonosseous implants.

Bone formation begins with chemotaxis of progenitor cells and their attachment to the demineralized matrix (27,41). This is followed by proliferation and differenation of attached cells into chondrocytes. Bone is formed when the cartilage matrix undergoes calcification and replacement by osteoid, which then mineralizes. Recent reports have identified specific proteins that appear to be responsible for the initiation of the different steps in this sequence. Weiss and Reddi (45,46) have demonstrated that the appearance of fibronectin on the surface of the demineralized bone matrix is essential to the induction of bone, and that antibodies to fibronectin prevent the normal process of endochondral ossification around the demineralized bone matrix. Fibronectin is a large adhesive glycoprotein with many biological properties. Both the cellular and plasma forms of fibronectin can bind cells and mediate their adhesion to collagen (10,49). We find that pre-treatment of the demineralized bone matrix grafts with plasma or with fibronectrin greatly enhances the onset and uniformity of the bone that forms in the ulnar defect. The effect of fibronectin as a chemotactic agent and as a competence factor in cell proliferation may also influence the distribution of cells within the graft impregnated with fibronectin (49). Proteins extracted from demineralized bone matrix have been reported to have both chemotectic and mitogenic activity (36). Shimizu et al. (34,35) demonstrated that some extracellular matrix proteins stimulate mitogenesis, while more recently Seyedin et al. (33) purified matrix proteins which stimulate a phenotypic change of myoblasts to chondroblasts. The factor(s) responsible for the subsequent calcification of cartilage and replacement by bone have not been identified. The full potential for bone induction probably resides in several proteins, each with a specific function or functions (27,41). Some, like fibronectin, may be circulating in the plasma, while others are extractable components of the bone matrix.

The strength of a bone graft during the repair process and at the conclusion of healing is of utmost clinical importance. Recently, attention has been directed to laboratory investigation of the strength of various types of grafts (4,9). Our study compares the strength of fibronectin coated demineralized bone matrix grafts with both normal and autologous bone grafts, and evaluates an attempt to increase the strength of the fibronectin coated demineralized bone matrix graft by augmenting the concentration of biologically active proteins on the matrix.

Sacrifice of the experimental animals at three months is too early to allow a determination of the ultimate strength of the grafted ulnas. It was, however, sufficient to show unequivocally that all the autografts and fibronectin coated demineralized bone matrix grafts healed in continuity with the cortex of the defect and remodeled to approximately normal ulnar anatomy. Union of the grafts with the cut ends of the cortex occurred by six weeks, and by twelve weeks the grafts had remodeled to resemble the normal ulna in size and shape, if not in thickness. Burchardt et al. (4) have indicated that lack of stress across the graft can precipitate resorption and failure of the graft. The segmental defect model used in this study, however, provided stability for the graft without compromising its healing.

The narrow range of variance in physical characteristics of bones from the right and left limbs of rabbits (25) allows relatively accurate comparison of the progress of healing with different grafts. The segmental defect model we used demonstrates subtle differences in strength, as seen between augmented and non-augmented grafts. The torsional strength of the non-operated ulnas was in the range expected based on previous reports of the strength of rabbit bone (25). The thin cortex of grafted bone seen in radiographs and histologic sections of fibronectin coated demineralized bone matrix grafts and autografts explains the decreased load to failure when compared with non-operated control ulnas. These results are in general agreement with those of Einhorn et al. (8) who evaluated demineralized bone matrix grafts of fermoral defects in rats. Radiographic and histologic similarities between fibronectin coated demineralized bone matrix grafts and autografts suggest that healing has progressed to approximately the same extent in these grafts. This is further supported by the mechanical testing results, which show no significant difference between these two grafts.

A significantly greater energy absorption is demonstrated by augmented fibronectin coated demineralized bone matrix grafts. However, the increase in torque to failure was found not to be statistically significant, and therefore it is not surprising that histology and radiography did not demonstrate appreciable differences between fibronectin coated demineralized bone matrix grafts and augmented fibronectin coated demineralized bone matrix grafts. The higher concentrations of biologically active proteins on the augmented fibronectin coated demineralized bone matrix grafts is conceivably responsible for increased stimulus to bone formation. Support for this interpretation comes from reports demonstrating that extractable matrix proteins exert concentration dependent effects on cell chemotaxis, mitogenesis, and proliferation (34,35,36). Closer investigation by histomorphometry might reveal differences in the course of healing between fibronectin coated demineralized bone matrix grafts and augmented fibronetin coated demineralized bone matrix grafts.

The results of this study are consistent with other studies that have used demineralized bone matrix grafts to repair various types of bone defects in animal models. Segmental long bone defects have been repaired with decalcified bone grafts in the rat fibulae by Oikarinen and Korhonen (24), and in the rabbit ulna by Tuli and Singh (36). Oikarinen (22) has also reported the use of decalcified bone matrix in experimental spine fusions in rabbits, and compared these grafts to fusions with autologous cancellous grafts and frozen allogeneic grafts. When evaluated by radiographic or histologic methods, demineralized bone grafts and autologous cancellous grafts yielded comparable results, while frozen allografts gave only incomplete fusions. Einhorn et al. (8) reported the healing of segmental femoral shaft defects in rats grafted with demineralized bone matrix. The grafts maintained position during healing and dictated the architecture of the repair, but were complicated by a 28% incidence of non-union. These non-augmented grafts were not treated with plasma or with fibronectin. Other reports using demineralized bone matrix prepared from cancellous bone demonstrate little or no bone induction potential (19,20).

Several investigators have studied the use of demineralized bone matrix or similar materials as bone grafts in humans. Reports from these clinical studies have been promising (12,32). Glowacki et al. (13) presented the short term followup of 34 patients in whom demineralized bone matrix was used to graft craniofacial reconstruction. Clinical and radiographic assessment showed apparent healing of large defects with rapid union. Iwata et al. (17) reported a series of 33 bone graft operations, for either lumbar spine instability or defects secondary to tumor resection, that were followed for a minimum of two years. Bone grafts were performed with demineralized bone matrix further extracted with lithium chloride, called autolyzed antigen-extracted allogenic bone. In three cases the benign tumor recurred locally, but in all other cases the graft had remodeled and was successfully united with existing bone when evaluated by radiography. Urist and Dawson (40) reported on forty intertransverse process fusions also performed with autolyzed antigen-extracted allogenic bone. When followed for one to nine years, they achieved 80% good to excellent results overall, but with a pseudoarthrosis rate of 12%.

Decalcified bone matrix may be a promising material for bone grafting. The matrix is easy to prepare and can be stored for extended periods. The new bone induced by fibronectin coated demineralized bone matrix grafts is mechanically as strong as bone formed after grafting with autologous cancellous bone. It would seem, therefore, that fibronectin coated demineralized bone matrix grafts are reasonable alternatives to the use of autografts, which as noted previously, can be in short supply. Advances in our understanding of the mechanisms of bone induction and in augmentation of this process may make grafting with demineralized bone or extracted biologically active proteins even more clinically attractive.

1. ANASTASSIADES, T., PUZIC, O., and PUZIC, R.: Effect of Solubilized Bone Matrix Components on Cultured Fibroblasts Derived from Neonatal Rat Tissues. Calcif. Tiss. Res., 26: 173-179, 1978.
2. BAADSGAARD, K.: Transplantation of Callus-Invaded Kiel Bone to Defect Pseudarthroses. Acta Orthop. Scandinav., 42: 122-130, 1971.
3. BOYNE, PHILIP J.: Induction of Bone Repair by Various Bone-Grafting Materials. In Heart Tissue Growth Repair and Remineralization, pp. 121-141. CIBA Foundation Symposium, Assoc. Scient. Pulb., Amsterdam, 1973.
4. BURCHARDT, HANS, JONES, HARDIN, GLOWCZEWSKIE, FRANK, RUDNER, CHARLES, and ENNEKING, WILLIAM F.: Freeze-dried Allogeneic Segmental Cortical-bone Grafts in Dogs. J. Bone and Joint Surg., 60-A: 1082-1090, 1978.
5. BURSTEIN, A. H., and FRANKEL, V. H.: A Standard Test For Laboratory Animal Bone, J. Biomechanics, 4: 155-158, 1971.
6. CUMMINE, JOHN, ARMSTRONG, LEE, and NADE, SYDNEY: Osteogenesis After Bone and Bone Marrow Transplantation. Acta. Orthop., 54: 235-241, 1983.
7. DUNCAN, DAVID B.: Multiple Range and Multiple-F Tests, Biometrics, 11: 1-42, 1955.
8. EINHORN, THOMAS A., LANE, JOSEPH M., BURSTEIN, ALBERT H., KOPMAN, CYNTHIA R., and VIGORITA, VINCENT J.: The Healing of Segmental Bone Defects Induced by Demineralized Bone Matrix. J. Bone and Joint Surg., 66-A: 274-279, 1984.
9. ENNEKING, WILLIAM F., BURCHARDT, HANS, PUHL, JAMES J., and PIOTROWSKI, GEORGE: Physical and Biological Aspects of Repair in Dog Cortical-bone Transplants. J. Bone and Joint Surg., 57-A: 237-252, 1975.
10. FERNYHOUGH, WILL, and PAGE, ROY C.: Attachment, Growth and Synthesis by Human Gingival Fibroblasts on Demineralized or Fibronectin-treated Normal and Diseased Tooth Roots. J. Periodontol, 54: 133-139, 1983.
11. FRIEDENSTEIN, ALEX J.: Precursor Cells of Mechanocytes. Int. Rev. Cytol., 47: 327-359, 1976.
12. GLOWACKI, JULIE, ALTOBELLI, DAVID, and MULLIKEN, JOHN B.: Fate of Mineralized and Demineralized Osseous Implants in Cranial Defects. Calcif. Tissue Int., 33: 71-76, 1981.
13. GLOWACKI, JULIE, KABAN, LEONARD B., MURRAY, JOSEPH E., FOLKMAN, JUDAH, and MULLIKEN, JOHN B.: Application of the Biological Principle of Induced Osteogenesis for Craniofacial Defects. The Lancet Ltd, May 2, 1981, pp. 959-962.
14. HAM, W., and HARRIS, W. ROBERT: Repair and Transplantation of Bone. In Biochemistry and Physiology of Bone, pp. 337-399. Edited by G. H. Bourne, Academic Press, publisher, New York, N.Y., 1971.
15. HANAMURA, HIROKATSU, HIGUCHI, YOSHINORI, NAKAGAWA, MASASHI, IWATA, HISASHI, NOGAMI, HIROSCHI, and URIST, MARSHALL R.: Solubilized Bone Morphogenetic Protein (BMP) from Mouse Osteosarcoma and Rat Demineralized Bone Matrix. Clin. Orthop. Rel. Res., 148: 281-290, 1980.
16. HEJNA, WILLIAM F., and RAY, ROBERT D.: Comparative Study of Bone Implants. Surgical Forum, 14: 448-450, 1963.
17. IWATA, HISASHI, HANAMURA, HIROKATSU, KANEKO, MASAYUKI, YASUHARA, NORIMASA, TERASHIMA, YOJI, KAJINO, GAKUJI, IDA, KUNIO, MABUCHI, YOSHIO, and NAKAGAWA, MASHAI: Chemosterilized Autolyzed Antigen-Extracted Allogeneic (AAA) Bone Matrix Gelatin for Repair of Defects from Excision of Benign Bone Tumors: A Preliminary Report. Clin. Orthop. Rel. Res., 154: 150-155, 1981.
18. MULLIKEN, JOHN B., and GLOWACKI, JULIE: Induced Osteogenesis for Repair and Construction in the Craniofacial Region. J. Plast. and Recon. Surg., 65: 553-555, 1980.
19. NADE, SYDNEY: Clinical Implications of Cell Function in Osteogenesis. A Reappraisal of Bone-Graft Surgery. Annals of the Royal College of Surgeons of England, 61: 189-194, 1979.
20. NADE, S., and BURWELL, R. G.: Decalcified Bone as a Substrate for Osteogenesis. J. Bone and Joint Surg., 59-B: 189-196, 1977.
21. NATHANSON, MARK A.: Proteoglycan Synthesis by Skeletal Muscle Undergoing Bone Matrix-directed Transformation into Cartilage In Vitro. J. Biol. Chem., 258: 10325-10334, 1983.
22. OIKARINEN, JORMA: Experimental Spinal Fusion with Decalcified Bone Matrix and Deep-frozen Allogeneic Bone in Rabbits. Clin. Orthop. Rel. Res., 162: 210-218, 1982.
23. OIKARINEN, JORMA, and KORHONEN, L. KALEVI: The Bone Inductive Capacity of Various Bone Transplanting Materials Used for Treatment of Experimental Bone Defects. Clin. Orthop. Rel. Res., 140: 208-215, 1979.
24. OIKARINEN, JORMA, and KORHONEN, L. KALEVI: Repair of Bone Defects by Bone Inductive Material. Acta. Orthop. Scand., 50: 21-26, 1979.
25. PAAVOLAINEN, PEKKA: Studies on Mechanical Strength of Bone. I. Torsional Strength of Normal Rabbit Tibio-Fibular Bone. Acta Orthop. Scand., 50: 497-505, 1978.
26. REDDI, A. H.: Cell Biology and Biochemistry of Endochondral Bone Development. Coll. Res., 1: 209-226, 1981.
27. REDDI, A. H.: Regulation of Local Differentiation of Cartilage and Bone by Extracellular Matrix: a Cascade Type Mechanism. In Limb Development and Regeneration, pp. 21-268. Alan R. Liss, Inc., publisher, New York, N.Y., 1983.
28. REDDI, A. H., and HUGGINS, C. B.: Biochemical Sequence in the Transformation of Fibroblasts into Cartilage and Bone, Proc., Natl. Acad. Sci. USA 69: 1601-1605, 1972.
29. SAMPATH, T. K., NATHANSON, M. A., and REDDI, A. H.: In Vitro Transformation of Mesenchymal Cells Derived from Embryonic Muscle into Cartilage in Response to Extracellular Matrix Components of Bone, Proc. Natl. Acad. Sci., USA, 81: 3419-3423, 1984.
30. SAMPATH, T. K., and REDDI, A. H.: Dissociative Extraction and Reconstitution of Extracellular Matrix Components Involved in Local Bone Differentiation. Proc. Natl. Acad. Sci., USA, 78(12): 7599-7603, 1981.
31. SAMPATH, T. K., and REDDI, A. H.: Homology of Bone-inductive Proteins from Human, Monkey, Bovine, and Rat Extracellular Matrix. Proc. Natl. Acad. Sci., USA, 80: 6591–6595, 1983.

32. SHARRAD, W. J. W., and COLLINS, D. H.: The Fate of Human Decalcified Bone Grafts. Proceed. Royal Soc. Med., Section of Orthopaedics, 54: 1101–1102, 1961.

33. SEYEDIN, SAEID M., THOMPSON, ANDREA Y., ROSEN, DAVID M., and PIEZ, Karl A.: In Vitro Induction of Cartilage-specific Macromolecules by a Bone Extract. J. Cell Biol., 97: 1950–1953, 1983.

34. SHIMIZU, NOBUYUKI, YOSHIKAQA, HIDEKI, TAKAOKA, Kunio, and ONO, KEIRO: Extracts of Human Cancellous Bone Stimulate DNA Synthesis in Osteoprogenitor Cells from Fetal Rats. Clin. Orthop. Rel. Res., 173: 222–228, 1983.

35. SHIMIZU, NOBUYUKI, YOSHIKAWA, HIDEKI, TAKAOKA, KUNIO, and ONO, KEIRO: Extracts of Cortical Bone from Adult Rats Stimulate DNA Synthesis in Osteoprogenitor Cells from Fetal Rats. Clin. Orthop. Rel. Res., 178: 252–257, 1983.

36. SOMERMAN, M., HEWITT, A. T., VARNER, H. H., SCHIFFMANN, E., TERMINE, J., and REDDI, A. H.: Identification of a Bone Matrix-derived Chemotactic Factor. Calcif. Tissue Int., 35: 481–485, 1983.

37. TAKAOKA, KUNIO, ONO, KEIRO, AMITANI, KATSUMASA, KISHIMOTO, RITSUKO, and NAKATA, YOZO: Solubilization and Concentration of a Bone-Inducing Substance from a Murine Osteosarcoma. Clin. Orthop. Rel. Res., 148: 274–280, 1980.

38. TULI, S. M., and SINGH, A. D.: The Osteoinductive Property of Decalcified Bone Matrix. An experimental study. J. Bone and Joint Surg., 60-B: 116–123, 1978.

39. URIST, MARSHALL, R.: New Bone Formation Induced in Postfetal Life by Bone Morphogenic Protein. In Mechanisms of Growth Control, pp. 406–434. Edited by R. O. Becker, Charles C. Thomas, publisher, Springfield, Ill., 1981.

40. URIST, MARSHALL R., and DAWSON, EDGAR: Intertransverse Process Fusion with the Aid of Chemosterilized Autolyzed Antigen-Extracted Allogeneic (AAA) Bone. Clin. Orthop. Rel. Res., 154: 97–113, 1981.

41. URIST, MARSHALL R., DeLANGE, ROBERT J., and FINERMAN, G. A. M.: Bone Cell Differentiation and Growth Factors. Science, 220: 680–686, 1983.

42. URIST, M. R., IWATA, H., CRECCOTT, P. L., DORFMAN, R. L., BOYD, S. D., MCDOWELL, R. M., and CHIEN, C.: Bone Morphogenesis in Implants of Insoluble Bone Gelatin. Proc. Natl. Acad. Sci. USA, 70: 511, 1973.

43. URIST, MARSHALL R., LIETZE, ARTHUR, MIZUTANI, HIDEKI, TAKAGI, KATSUMASA, TRIFFITT, JAMES T., AMSTUTZ, JULIE, DeLANGE, ROBERT, TERMINE, JOHN, and FINERMAN, GEORGE A. M.: A Bovine Low Molecular Weight Bone Morphogenetic Protein (BMP) Fraction. Clin. Orthop. Rel. Res., 162: 219–232, 1982.

44. URIST, MARSHALL R., SATO, KEIJI, BROWNELL, ANNA G., MALININ, THEODORE I., LIETZE, ARTHUR, HUO, YONG-KANG, PROLO, DONALD J., OKLUND, SALLY, FINERMAN, GERALD A. M., and DeLANGE, ROBERT J.: Human Bone Morphogenetic Protein (hBMP). Proc. Soc. Exp. Biol. Med., 173: 194–199, 1983.

45. WEISS, ROY E., and REDDI, A. H.: Synthesis and Localization of Fibronectin During Collagenous Matrix-mesenchymal Cell Interaction and Differentiation of Cartilage and Bone In Vivo. Proc. Natl. Acad. Sci., USA, 77: 2074–2078, 1980.

46. WEISS, ROY E., and REDDI, A. H.: Appearance of Fibronectin During the Differentiation of Cartilage, Bone, and Bone Marrow. J. Cell Biol., 88: 630–636, 1981.

47. WHITE, AUGUSTUS A., PANJABI, MANOHAR M., and SOUTHWICK, WAYNE O.: The Four Biomechanical Stages of Fracture Repair. J. Bone. Joint Surg., 59-A: 188–192, 1977.

48. WITTBJER, JAN, PALMER, BJORN, ROHLIN, MADELEINE, and THORNGREN, KARL-GORAN: Osteogenetic Activity in Composite Grafts of Demineralized Compact Bone and Marrow. Clin. Orthop. Rel. Res., 173: 229–237, 1983.

49. YAMADA, KENNETH M.: Cell Surface Interactions with Extracellular Materials. Ann. Rev. Biochem., 52: 761–799, 1983.

50. ZADEK, R. E., and ROBINSON, R. A.: The Healing of an Ostealperiosteal Discontinuity of Standard Length in Skeletally Mature and Immature Canine Radii. The Healing of Osseaus Tissue. A workshop sponsored by The Committee on the Skeletal System. Division of Medical Sciences. N.A.S.-N.R.C. 22–23 October, 1965. Published 1967, pp. 9–22.

FIGURE LEGENDS

FIG. 1: Sodium dodecyl sulfate polyacrylamide gel electrophoresis of guanidinium hydrochloride extract of demineralized bone matrix. The guanidinium hydrochloride extract was dialyzed, then lyophilized and approximately 100 μg of this material analyzed on a 12.5% polyacrylamide slab gel in the presence (+) or absence (−) of the disulfide bond reducing agent dithiothreitol (DTT). Proteins were stained with Coomassie Blue. The horizontal bars indicate the migration positions of globular protein standards with their corresponding molecular weights. The arrows point to bands which correspond to the α1 and α2 chains of type I collagen.

FIG. 2: Radiographs taken fourteen days after demineralized bone matrix grafting of bilateral ulnar defects:
(a) Defect grafted with demineralized bone matrix soaked in Lactated Ringer's solution prior to implantation. Minimal repair is seen across the defect. Healing in these grafts failed to progress. Our observation was that no calcification was seen in demineralized bone matrix grafts until twenty-one days, and a non-union would be present at three months.
(b) Defect grafted with demineralized bone matrix pretreated with autologous citrated plasma (fibronectin coated demineralized bone matrix graft). The calcified graft is seen bridging the defect. The separation between graft and cortex was a typical finding at this stage. As healing progressed, the graft would extend across this distance and join firmly with the cortex. We feel that this separation is probably due to a small amount of motion present in the early stages of healing. This pattern of repair supports the contention that demineralized bone matrix does not act merely as a scaffold for the ingrowth of bone from the ends of the defect, but instead contributes to healing by inducing bone formation. No non-unions were formed in fibronectin coated demineralized bone matrix grafts.

FIG. 3: Progression of Healing: Radiographic examination of Group II. Segmental defects grafted with autologous cancellous bone or with fibronectin coated demineralized bone matrix were x-rayed immediately postoperatively and at six and twelve weeks thereafter: fibronectin coated demineralized bone matrix graft (a,c,e) and autograft (b,d,f). Radiographs taken immediately after implantation of graft material into the bilateral two centimeter defects demonstrate that the fibronectin coated demineralized bone matrix graft is radiolucent (FIG. 3a). At six weeks after grafting a fine, irregular trabecular pattern is seen (FIG. 3c). The graft fills the defect and extends proximally and distally, fusing to the ulnar cortex. By twelve weeks (FIG. 3e), the fibronectin coated demineralized bone matrix graft has remodeled to approximate the normal shape of the ulna, and the ends of the graft are fused to the normal cortex. Although the graft cortex is irregular and thinner than the normal ulna cortex, there is no evidence of pseudoarthrosis. The postoperative radiograph shows that the autograft completely fills the ulnar defect (FIG. 3b). After six weeks, marked changes occured in this graft as well. The irregular graft fills the defect with a calcified mass that appears to be bone (FIG. 3d). At twelve weeks the autografted ulna has a radiographic appearance not unlike the fibronectin coated demineralized bone matrix graft (FIG. 3f). Both grafts have remodeled extensively to approach the size and configuration of the normal ulna, with some cortical irregularity and thinning.

FIG. 4: Radiographic comparison of grafted ulnas after sacrifice at twelve weeks:
Group I: a non-operated control ulna, b: fibronectin coated demineralized bone matrix
Group II: c: fibronectin coated demineralized bone matrix, d: autograft
Group III: e: fibronectin coated demineralized bone matrix, f: augmented fibronectin coated demineralized bone matrix
Group IV: g: fibronectin coated demineralized bone matrix, h: non-grafted control ulna Although marked radiographic differences in graft healing can be seen between ulnas from different groups, the differences between right and left ulnas in the same animal are slight. This was typical for all animals.

FIG. 6: Load-deformation curves for typical animals in each group. For each animal the curve for the fibronectin coated demineralized bone matrix grafted ulna and the contralateral control ulna is plotted on the same graph.
Group I
  Thick line—fibronectin coated demineralized bone matrix
  Thin line—Normal
Group II
  Thick line—fibronectin coated demineralized bone matrix
  Thin line—Autograft
Group III
  Thick line—fibronectin coated demineralized bone matrix
  Thin line—Augmented fibronectin coated demineralized bone matrix

TABLE 1

| GROUPS | NUMBER | SURGERY | GRAFTS EVALUATED |
|---|---|---|---|
| I | 12 | unilateral 2 cm. ulnar defect | Fibronectin coated demineralized bone matrix grafts vs normal ulna controls |
| II | 11 | bilateral 2 cm. ulnar defects, iliac crest graft harvest | Fibronectin coated demineralized bone matrix graft vs autologous cancellous graft |
| III | 12 | bilateral 2 cm. ulnar defects | Fibronectin coated demineralized bone matrix graft vs augmented fibronectin coated demineralized bone matrix graft |
| IV | 12 | bilateral 2 cm. ulnar defects | Fibronectin coated demineralized bone matrix grafts vs non-grafted controls |

TABLE 2

Amino acid composition[1] of (a) demineralized bone matrix, (b) extract: material soluble in guanidinium hydrochloride, (c) residue: insoluble material after extraction of demineralized bone matrix with guanidinium hydrochloride. Values are expressed as residues per 1000 amino acid residues.

|  | (a) | (b) | (c) |
|---|---|---|---|
| Hydroxyproline | 99 | 11 | 100 |
| Aspartic acid | 52 | 141 | 53 |
| Threonine | 19 | 39 | 19 |
| Serine | 36 | 52 | 39 |
| Glutamic acid | 75 | 157 | 83 |
| Proline | 120 | 51 | 126 |
| Glycine | 311 | 123 | 297 |
| Alanine | 109 | 87 | 113 |
| Cystine | 1.3 | 19 | 0.4 |
| Valine | 22 | 41 | 20 |
| Methionine | 11 | 12 | 11 |
| Isoleucine | 6.1 | 18 | 5.6 |
| Leucine | 27 | 75 | 27 |
| Tyrosine | 5.6 | 30 | 5.1 |
| Phenylalanine | 15 | 31 | 14 |
| Histidine | 6.9 | 25 | 6.0 |
| Hydroxylysine | 6.8 | 2.9 | 8.8 |
| Lysine | 29 | 45 | 24 |
| Arginine | 49 | 43 | 49 |

[1]Amino acid analyses were performed on salt free lyophilized material hydrolyzed in constant boiling HCl for 24 h at 108° C. in vacuo. A Beckman 119 analyzer was used and no corrections were made for losses due to destruction of amino acids during hydrolysis.

TABLE 3

MECHANICAL PROPERTIES OF NORMAL AND GRAFTED ULNAS DETERMINED BY STANDARD TORSIONAL TEST

| | | TORQUE (Newton-meters) | ENERGY (Newton-meter-degrees) | ANGLE (Degrees) |
|---|---|---|---|---|
| GROUP I (12 animals) | AVERAGE VALUES | | | |
| | FN-DBM grafted ulnas | 0.40 | 3.34 | 11.6 |
| | Normal control ulnas | 0.82 | 7.88 | 16.2 |
| | mean difference[1] | −0.43 | −5.09 | −5.16 |
| | Standard error | 0.07 | 0.81 | 1.85 |
| | | Normal > FN-DBM $p^2 < .001$ | Normal > FN-DBM $p < .001$ | Normal > FN-DBM $p < .01$ |
| GROUP II (11 animals) | AVERAGE VALUES | | | |
| | FN-DBM grafted ulnas | 0.46 | 3.36 | 12.1 |
| | Autografted ulnas | 0.32 | 3.51 | 13.6 |
| | Mean difference | 0.14 | −0.14 | −1.81 |
| | Standard error | 0.07 | 0.92 | 4.58 |
| | | FN-DBM > Autograft N.S. | Autograft > FN-DBM N.S. | Autograft > FN-DBM N.S. |
| GROUP III (12 animals) | AVERAGE VALUES | | | |
| | FN-DBM grafted ulnas | 0.34 | 2.33 | 10.7 |
| | Augmented FN-DBM grafted ulnas | 0.45 | 3.71 | 15.6 |
| | Mean difference | −0.11 | −1.37 | −4.38 |
| | Standard error | 0.06 | 0.41 | 1.91 |
| | | Aug FN-DBM > FN-DBM N.S. | Aug FN-DBM > FN-DBM $p < .01$ | Aug FN-DBM > FN-DBM $p < .04$ |
| GROUP IV (12 animals) | FN-DBM Non-grafted[3] | 0.43 — | 3.59 — | 10.8 — |

[1]Mean of the differences between the contralatoral sides.
[2]$p > .05$ = not significant (N.S.)
[3]Non-grafted defects did not heal or demonstrate detectable mechanical strength

We claim:

1. The process of grafting material from milled bone, comprising, augmenting the bone proteins of a first quantity of milled bone by dialyzing from solution guanidine-extracted bone proteins from a second quantity of milled bone, adding the extracted bone proteins extracted from the second quantity of milled bone to the first quantity of milled bone, removing unbound bone proteins from the augmented first quantity, and lyophilizing the augmented first quantity of milled bone, coating the augmented first quantity of milled bone with anti-coagulated plasma containing plasma proteins, and removing unbound plasma proteins from the coated augmented first quantity of milled bone by rinsing.

* * * * *